United States Patent
Miki et al.

(10) Patent No.: US 6,610,896 B2
(45) Date of Patent: Aug. 26, 2003

(54) PROCESS FOR PRODUCTION OF PERFLUOROALKADIENES

(75) Inventors: Jun Miki, Settsu (JP); Hitoshi Yoshimi, Settsu (JP); Hirokazu Aoyama, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 10/169,076

(22) PCT Filed: Dec. 28, 2000

(86) PCT No.: PCT/JP00/09392

§ 371 (c)(1), (2), (4) Date: Jul. 5, 2002

(87) PCT Pub. No.: WO01/51436

PCT Pub. Date: Jul. 19, 2001

(65) Prior Publication Data

US 2002/0193643 A1 Dec. 19, 2002

(30) Foreign Application Priority Data

Jan. 12, 2000 (JP) ......................................... 2000-003823

(51) Int. Cl.$^7$ .......................... C07C 17/00; C07C 21/18; C07C 17/25; C07C 19/08
(52) U.S. Cl. ........................................ 570/158; 570/136
(58) Field of Search .................................. 570/136, 158, 570/153, 155, 156

(56) References Cited

FOREIGN PATENT DOCUMENTS

| EP | 0205892 A1 | 12/1986 |
|----|------------|---------|
| EP | 0270956 A1 | 6/1988 |

OTHER PUBLICATIONS

Blancou, H., et al; "Reactivite des perfluorohalogenoalcanes en presence de couples metalliques–II"; Tetrahedoron, vol. 33, No. 16 (1977) pp. 2061–2067. (see Search Report).
International Search Report dated Mar. 13, 2001.

*Primary Examiner*—Samuel Barts
*Assistant Examiner*—Elvis O. Price
(74) *Attorney, Agent, or Firm*—Armstrong, Westerman & Hattori, LLP

(57) ABSTRACT

A process for preparing a perfluoroalkadiene compound of formula (I)

$$CF_2=CF—(CF_2)_{n-4}—CF=CF_2 \qquad (I)$$

(wherein n is an integer from 4 to 20) by the deiodofluorination of a compound of formula (II)

$$I—(CF_2)_n—I \qquad (II)$$

(wherein n is as defined above),
characterised in that said deiodofluorination is conducted in the presence of metallic zinc and a nitrogen-containing organic compound.

4 Claims, No Drawings

PROCESS FOR PRODUCTION OF PERFLUOROALKADIENES

TECHNICAL FIELD

The present invention relates to a process for preparing perfluoroalkadienes with terminal double bonds.

BACKGROUND ART

Perfluorobutadiene is useful as a dry etching gas (Chemical Week, Oct. 13, 1999, page 47) and a monomer for the production of fluoroelastomers (Japanese Unexamined Patent Publication Nos. 26240/1987 and 141935/1988) and among other applications.

The methods disclosed in Japanese Unexamined Patent Publication Nos. 26240/1987 and 141935/1988 for preparing perfluoroalkadiene compound of formula (I)

(wherein n is an integer of 4 to 20) involve the deiodofluorination of compound of formula (II)

(wherein n is the same value as above) using Mg, Zn, Cd or Li organometallic compound, at temperatures from −80° C. to +150° C. in the presence of a neutral hydrocarbon solvent. However, these organometallic compounds (n-butyl lithium, ethyl magnesium bromide, etc.) have the drawback of being expensive and difficult-to-handle reagents which decompose readily.

DISCLOSURE OF THE INVENTION

An object of the present invention is to provide an easy method for preparing perfluoroalkadienes without the use of expensive and difficult-to-handle reagents.

The inventors, as a result of their research concerning production processes of compound of formula (I) based on the deiodofluorination of compound of formula (II), found unexpectedly that target compound of formula (I) could be obtained with high selectivities and yields by contacting a compound of formula (II) with metallic zinc and a nitrogen-containing organic compound, instead of organometallic compound like n-butyl lithium, etc.

The present invention relates to the items 1–4 listed below:

Item 1. A process for preparing perfluoroalkadiene compound of formula (I)

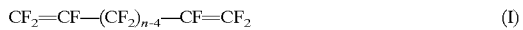

(wherein n is an integer of 4 to 20) by the deiodofluorination of compound of formula (II)

(wherein n is as defined above), characterised in that the deiodofluorination is carried out in the presence of metallic zinc and a nitrogen-containing organic compound.

Item 2. The process according to item 1 wherein the nitrogen-containing organic compound is at least one compound selected from the group consisting of N,N-dimethyl formamide, N,N-dimethyl acetamide, N,N-diisopropyl formamide, triethylamine, pyridine, methyl pyridine, N-methyl-2-pyrrolidone, quinoline and methyl quinoline.

Item 3. The process according to item 2 wherein the nitrogen-containing organic compound is at least one compound selected from the group consisting of N,N-dimethyl formamide and N-methyl-2-pyrrolidone.

Item 4. The process described in item 1, characterised in that the deiodofluorination is carried out in an inert solvent.

In the process according to the present invention, the deiodofluorination of compound of formula (II) I—$(CF_2)_n$—I (wherein n is an integer of 4 to 20) may be carried out in the presence of metallic zinc and a nitrogen-containing organic compound.

Usable nitrogen-containing organic compounds are not specifically limited, and any usual organic solvent used in organic reactions and containing a nitrogen atom (nitrogen-containing organic solvent) may be used. For example, amides (N,N-dimethyl formamide (DMF), N,N-dimethyl acetamide, N,N-diisopropyl formamide, etc.), amines (triethyl amine, etc.), pyridines (pyridine, methyl pyridine, etc.), pyrrolidones (N-methyl-2-pyrrolidone (NMP), etc.), quinolines (quinoline, methyl quinoline, etc.) and the like. Among these compounds, amides and pyrrolidones are preferable, DMF and NMP are more preferable. These nitrogen-containing organic compounds can be used singly or in combination of two or more.

The amount of a nitrogen-containing organic compound to be used is not specifically limited so far as the effects of the present invention are obtained, however, they range usually from about 0.01 to about 100 mol, preferably from about 0.5 to about 10 mol per 1 mol of compound of formula (II). When the amount of a nitrogen-containing organic compound is within the above range, high conversion rates are obtained, which results in an economic advantage.

As regards metallic zinc, commercially available metallic zinc powder can be used. The amount of metallic zinc to be used is not specifically limited so far as the effects of the present invention are obtained, however, it ranges usually from about 0.01 to about 100 mol, preferably from about 0.5 to about 10 mol per 1 mol of compound of formula (II). When the amount of metallic zinc is within the above range, high conversion rates are achieved, which results in an economic advantage.

The reaction temperature may vary from about −80° C. to about +200° C., preferably from about 80 to about 160° C. When the reaction temperature is within the range of 80 to 160° C., the reaction rate is high enough, with sufficient conversion rates, being therefore desirable from an economic point of view.

The mixture of the compound of formula (II) with the metallic zinc and the nitrogen-containing organic solvent may be carried out in any order; however, higher conversion rates are achieved if the nitrogen-containing organic compounds are added dropwise to a liquid mixture of compound of formula (II) and metallic zinc.

Since the deiodofluorination of compounds of formula (II) is an exothermic reaction, it is preferable to dilute the compounds of formula (II) and/or the nitrogen-containing organic compound in an inert solvent (i.e., a solvent that does not take part in the reaction) prior to the deiodofluorination, in order to control the local heat release.

Examples of the inert solvents are perfluoro solvents (more specifically, chain or cyclic perfluoroalkanes, perfluoroamines, or perfluoroethers containing about 5 to about 15 carbon atoms), etc. Commercially available perfluoro solvents are, for example, FC-43 and FC-70 (brand name, 3M). The appropriate amount of inert solvent can be determined without specific limitations, but usually about 0.1 g to about 20 g, preferably from about 1 g to about 5 g of solvent is used for 1 g of compound of formula (II).

The reaction time is not specifically limited and may be determined in accordance with other reaction conditions, such as the reaction temperature, though it normally ranges from about 1 minute to about 5 hours, preferably from about 10 minutes to about 1 hour.

The reaction pressure is not specifically limited, although the reaction is conducted usually at normal pressure or reduced pressure (for example, from about 0.05 to about 0.2 MPa).

The perfluoroalkadienes thus obtained can be separated from the reaction mixture or purified by means of conventional separation or purification methods.

The present invention provides thus an easy method for preparing perfluoroalkadienes without using expensive and difficult-to-handle reagents.

BEST MODE FOR CARRYING OUT THE INVENTION

The present invention is explained more in detail by means of the examples below, however, the invention is not to be limited to these examples.

EXAMPLE 1

15.0 g of I—$CF_2CF_2CF_2CF_2$—I and 4.1 g (2 eq) of zinc powder were placed in an 100 ml eggplant flask equipped with a Dimroth condenser and connected to a dry ice cold trap, the mixture was then heated slowly, under stirring, up to an inner temperature of 120° C. by a mantle-heater. The mixture was kept at this temperature for 30 minutes. Next, 4.9 g (2 eq) of anhydrous DMF were added slowly from a dropping funnel (in order to control the release of heat) and the reaction continued. After about 30 minutes, 4.4 g of gas were recovered in the trap. The results of the analysis of the gas composition were: perfluorobutadiene ($CF_2$=CF—CF=$CF_2$) 65%, 1327 pcy ($CF_2H$—$CF_2$—CF=$CF_2$) 23%, perfluorocyclobutane 7%, 338 pcc ($CF_2H$—$CF_2$—$CF_2$—$CF_2H$) 2% (other by-products making up the remaining 3%). After separating the gas by means of conventional methods, 2.9 g of the target compound, perfluorobutadiene, were obtained.

EXAMPLE 2

40.0 g of I—$CF_2CF_2CF_2CF_2$—I, 120 g of perfluoro solvent (FC-70 from 3M) and 23 g (4 eq) of zinc powder were placed in an 500 ml eggplant flask equipped with a Dimroth condenser and connected to a dry ice cold trap, the mixture was then heated slowly, under stirring, up to an inner temperature of 140° C. by a mantle-heater. The mixture was kept at this temperature for 30 minutes. Next, 25.7 g (4 eq) of anhydrous DMF were added slowly from a dropping funnel (in order to control the release of heat) and the reaction continued. After about 30 minutes, 10.4 g of gas were recovered in the trap. The results of the analysis of the gas composition were: perfluorobutadiene ($CF_2$=CF—CF=$CF_2$) 88%, 1327 pcy ($CF_2H$—$CF_2$—CF=$CF_2$) 7%, perfluorocyclobutane 1%, 338 pcc ($CF_2H$—$CF_2$—$CF_2$—$CF_2H$) 1% (other by-products making up the remaining 3%). After separating the gas by means of conventional methods, 9.2 g of the target compound, perfluorobutadiene, were obtained.

EXAMPLE 3

20.0 g of I—$CF_2CF_2CF_2CF_2$—I, 40.0 g of perfluoro solvent (FC-43 from 3M) and 5.7 g (2 eq) of zinc powder were placed in an 200 ml eggplant flask equipped with a Dimroth condenser and connected to a dry ice cold trap, the mixture was then heated slowly, under stirring, up to an inner temperature of 140° C. by a mantle-heater. The mixture was kept at this temperature for 30 minutes. Next, 8.7 g (2 eq) of NMP (N-methyl-2-pyrrolidone) were added slowly from a dropping funnel (in order to control the release of heat) and the reaction continued. After about 30 minutes, 4 g of gas were recovered in the trap. The results of the analysis of the gas composition were: perfluorobutadiene ($CF_2$=CF—CF=$CF_2$) 85%, 1327 pcy ($CF_2H$—$CF_2$—CF=$CF_2$) 10%, perfluorocyclobutane 3%, 338 pcc ($CF_2H$—$CF_2$—$CF_2$—$CF_2H$) 2%. After separating the gas by means of conventional methods, 3.4 g of the target compound, perfluorobutadiene, were obtained.

EXAMPLE 4

20.0 g of I—$CF_2CF_2CF_2CF_2$—I, 40.0 g of perfluoro solvent (FC-70 from 3M) and 5.7 g (2 eq) of zinc powder were placed in an 200 ml eggplant flask equipped with a Dimroth condenser and connected to a dry ice cold trap, the mixture was then heated slowly, under stirring, up to an inner temperature of 140° C. by a mantle-heater. The mixture was kept at this temperature for 30 minutes. Next, 11.3 g (2 eq) of quinoline were added slowly from a dropping funnel (in order to control the release of heat) and the reaction continued. After about 30 minutes, 2.5 g of gas were recovered in the trap. The results of the analysis of the gas composition were: perfluorobutadiene ($CF_2$=CF—CF=$CF_2$) 85%, 1327 pcy ($CF_2H$—$CF_2$—CF=$CF_2$) 6%, perfluorocyclobutane 6%, 338 pcc ($CF_2H$—$CF_2$—$CF_2$—$CF_2H$) 3%. After separating the gas by means of conventional methods, 2.1 g of the target compound, perfluorobutadiene, were obtained.

EXAMPLE 5

200 g of I—$CF_2CF_2CF_2CF_2$—I and 57 g (2 eq) of zinc powder were placed in an 1,000 ml eggplant flask equipped with a Dimroth condenser and connected to a dry ice cold trap, the mixture was then heated slowly, under stirring, up to an inner temperature of 120° C. by a mantle-heater. The mixture was kept at this temperature for 30 minutes. Next, 128 g (4 eq) of anhydrous DMF were added slowly from a dropping funnel (in order to control the release of heat) and the reaction continued. After about 30 minutes, 60.6 g of gas were recovered in the trap. The results of the analysis of the gas composition were: perfluorobutadiene ($CF_2$=CF—CF=$CF_2$) 90%, 1327 pcy ($CF_2H$—$CF_2$—CF=$CF_2$) 6%, perfluorocyclobutane 1%, 338 pcc ($CF_2H$—$CF_2$—$CF_2$—$CF_2H$) 1% (other by-products making up the remaining 2%). After separating the gas by means of conventional methods, 54.5 g of the target compound, perfluorobutadiene, were obtained.

EXAMPLE 6

5.0 kg (11 mol) of I—$CF_2CF_2CF_2CF_2$—I, 10 kg of perfluoro solvent (FC-43, from 3M) and 1.73 kg (26 mol) of zinc powder (#48005-01 of Kanto Chemical Co., grade >85%) were added to a 10L stainless reaction vessel connected to a reflux condenser and a dry ice cold trap; the temperature was raised under stirring up to 120° C. and then kept at that temperature for 30 minutes. Next, 0.80 kg (11 mol) of DMF were added dropwise over 2 hours, while monitoring the heat released by the reaction all along. The reaction continued for a further 6 hours, and then the liquid collected in the cold trap was analysed. 1.5 kg of the target compound, perfluorobutadiene, were obtained.

What is claimed is:

1. A process for preparing a perfluoroalkadiene compound of formula (I)

$$CF_2=CF-(CF_2)_{n-4}-CF=CF_2 \quad (I)$$

(wherein n is an integer of 4 to 20) by the deiodofluorination of a compound of formula (II)

$$I-(CF_2)_n-I \quad (II)$$

(wherein n is as defined above),
characterised in that said deiodofluorination is conducted in the presence of metallic zinc and a nitrogen-containing organic compound.

2. The process according to claim 1 wherein said nitrogen-containing organic compound is at least one compound selected from the group consisting of N,N-dimethylformamide, N,N-dimethylacetamide, N,N-diisopropyl formamide, triethyl amine, pyridine, methyl pyridine, N-methyl-2-pyrrolidone, quinoline and methyl quinoline.

3. The process according to claim 2 wherein said nitrogen-containing organic compound is at least one compound selected from the group consisting of N,N-dimethylformamide and N-methyl-2-pyrrolidone.

4. The process according to claim 1 characterised in that said deiodofluorination is conducted in an inert solvent.

* * * * *